United States Patent
Cano

(10) Patent No.: US 6,264,663 B1
(45) Date of Patent: Jul. 24, 2001

(54) DEVICE FOR REMOVING SOLID OBJECTS FROM BODY CANALS, CAVITIES AND ORGANS INCLUDING AN INVERTABLE BASKET

(75) Inventor: Gerald G. Cano, Penn Hills, PA (US)

(73) Assignee: Metamorphic Surgical Devices, LLC, Pittsburgh, PA (US)

( * ) Notice: Subject to any disclaimer, the term of this patent is extended or adjusted under 35 U.S.C. 154(b) by 0 days.

(21) Appl. No.: 09/013,178

(22) Filed: Jan. 26, 1998

Related U.S. Application Data

(63) Continuation-in-part of application No. 08/539,875, filed on Oct. 6, 1995, now Pat. No. 5,779,716.

(51) Int. Cl.⁷ .......................... A61B 17/22; A61B 17/12
(52) U.S. Cl. .......................... 606/114; 606/110; 606/113
(58) Field of Search .................... 606/110, 113, 606/114, 127

(56) References Cited

U.S. PATENT DOCUMENTS

| | | | |
|---|---|---|---|
| 2,856,933 | 10/1958 | Hildebrand et al. | 128/305 |
| 3,181,533 | 5/1965 | Heath | 128/320 |
| 4,665,906 | 5/1987 | Jervis | 128/92 YN |
| 5,067,957 | 11/1991 | Jervis | 606/108 |
| 5,147,371 | 9/1992 | Washington et al. | 606/127 |
| 5,188,111 | 2/1993 | Yates et al. | 128/657 |
| 5,190,542 | 3/1993 | Nakao et al. | 606/47 |
| 5,190,546 | 3/1993 | Jervis | 606/78 |
| 5,190,555 | 3/1993 | Wetter et al. | 606/114 |
| 5,192,284 | 3/1993 | Pleatman | 606/114 |
| 5,192,286 | 3/1993 | Phan et al. | 606/127 |
| 5,201,740 | 4/1993 | Nakao et al. | 606/113 |
| 5,201,741 | 4/1993 | Dulebohn | 606/113 |
| 5,215,521 | 6/1993 | Cochran et al. | 604/22 |
| 5,234,439 | 8/1993 | Wilk et al. | 606/114 |
| 5,279,539 | 1/1994 | Bohan et al. | 600/37 |
| 5,312,416 | 5/1994 | Spaeth et al. | 606/114 |
| 5,312,417 | 5/1994 | Wilk | 606/114 |
| 5,341,815 | 8/1994 | Cofone et al. | 128/749 |
| 5,352,184 | 10/1994 | Goldberg et al. | 600/37 |
| 5,354,303 | 10/1994 | Spaeth et al. | 606/128 |
| 5,366,460 | 11/1994 | Eberbach | 606/151 |
| 5,368,597 | 11/1994 | Pagedas | 606/114 |
| 5,480,404 | 1/1996 | Kammerer et al. | 606/113 |
| 5,486,182 | 1/1996 | Nakao et al. | 606/114 |
| 5,486,183 | 1/1996 | Middleman et al. | 606/127 |
| 5,611,803 | * 3/1997 | Heaven et al. | 606/114 |
| 5,695,519 | 12/1997 | Summers et al. | 606/200 |
| 5,853,374 | * 12/1998 | Hart et al. | 600/562 |

FOREIGN PATENT DOCUMENTS

WO 96/01591 * 1/1996 (WO) .................................. 606/114

* cited by examiner

Primary Examiner—Mickey Yu
Assistant Examiner—Benjamin K. Koo
(74) Attorney, Agent, or Firm—Webb Ziesenheim Logsdon Orkin & Hanson, P.C.

(57) ABSTRACT

The present invention is directed to a surgical instrument used in minimally invasive procedures performed under either direct, endoscopic, fluoroscopic, or other visualization. The surgical instrument includes a frame which can be retracted into and extended from a sheath to form a loop and a sack having a mouth that is attached to the loop. The sack is used to encircle and capture foreign objects in body canals, cavities or organs. The wire frame is formed of a shape-memory-effect alloy wire in a super elastic state and previously trained to form the loop, the loop forming when the said wire frame is extended beyond the sheath. An invertor is connected to a closed end of the sack for urging the closed end of the sack toward the mouth of the sack.

19 Claims, 7 Drawing Sheets

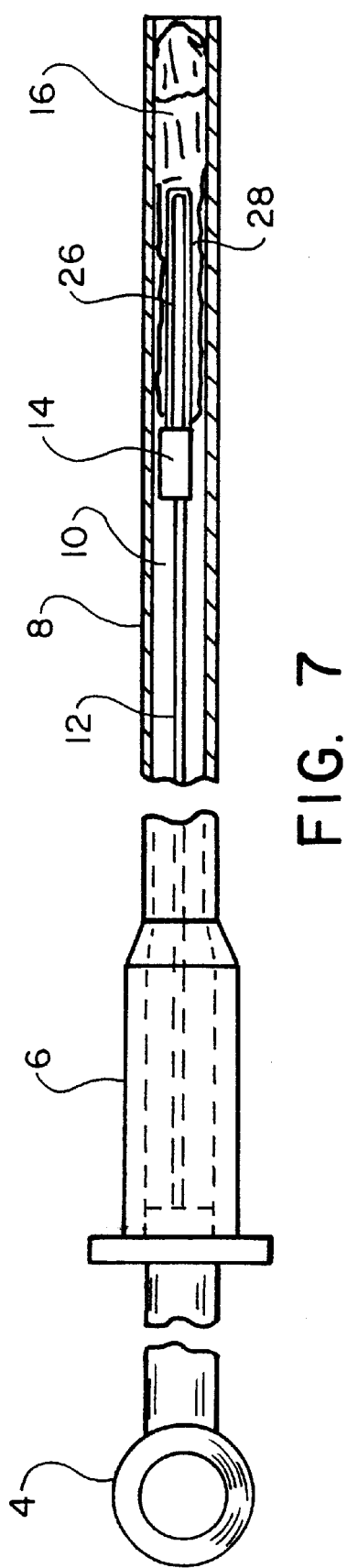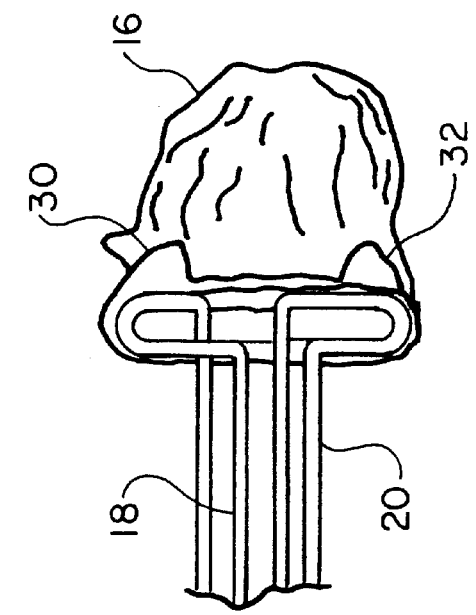

DEVICE FOR REMOVING SOLID OBJECTS FROM BODY CANALS, CAVITIES AND ORGANS INCLUDING AN INVERTABLE BASKET

CROSS REFERENCE TO RELATED APPLICATION

This application is a continuation-in-part of application Ser. No. 08/539,875 filed on Oct. 6, 1995 now U.S. Pat. No. 5,779,716.

BACKGROUND OF THE INVENTION

1. Field of the Invention

This invention relates generally to surgical instruments used in minimally invasive procedures performed under either direct, endoscopic, fluoroscopic or other visualization and more specifically to a surgical instrument used to capture and remove foreign objects or excised tissue from body canals, cavities, and organs.

2. Background of the Invention

Existing surgical devices for grasping and removing foreign objects from body organs or cavities include mechanically actuated forceps, mechanically actuated snares or mechanically actuated baskets. Each of these surgical devices may be positioned within the body under direct, endoscopic, fluoroscopic or other visualization.

Mechanically actuated forceps usually have two to four arms or prongs, each arm typically ending with a hooked tip. Each arm is typically composed of flat or round stainless steel and is connected at the end opposite the tip to a handle used to position and grasp. Most mechanically actuated forceps include an inner and outer sheath. The outer sheath is fixed with respect to the handle and the inner sheath may be advanced from or retracted into the outer sheath. When the inner sheath is retracted into the outer sheath, the arms spread from each other, allowing the forceps to be advanced toward and around an object within the body sought to be captured or removed. The arms of the forceps are then tightly closed about the object by extending the inner sheath from the outer sheath in the direction of the tips, whereupon the arms are urged together to encircle and grasp the object sought to be captured or removed.

Mechanically actuated snares preferably include a loop of wire enclosed within a sheath. The loop of wire can be extended beyond the sheath to form an oval opening. The size of the oval opening is controlled by the length of wire advanced beyond the end of the sheath. In use, after the snare is positioned adjacent the object, the wire is advanced beyond the end of the sheath until a loop larger than the object is formed. The loop is then positioned until the plane of the loop encircles the object. The sheath is then advanced and the wire retracted so that the loop closes around and ensnares the object.

Several of the snare-type surgical devices also incorporate a sack associated with the snare to trap the object to be captured or removed. One example includes U.S. Pat. No. 5,190,555 which includes a sack of a flexible material and further requires a drawstring to open and close the sack. Another example is U.S. Pat. No. 5,192,286 which includes a net which can be collapsed to facilitate introduction into the body lumen and opened in situ to permit capture and retrieval of an object therein. The net is opened by a flexible loop member. Another example is U.S. Pat. No. 5,354,303 which includes a flexible sac and a resilient or spring loaded rim member disposed about the opening to urge the opening to an open configuration when deployed in the body cavity.

Mechanically actuated baskets typically include three to six wires enclosed within a sheath. The wires are joined at a first end with a handle and are joined at a second, distal, end to each other. Advancing the wires beyond the sheath forms a basket. The volume of the basket is controlled by the length the wires are advanced beyond the sheath. In use, the closed basket is positioned adjacent the object to be captured or removed and a portion of the wire is advanced beyond the sheath to form a basket of sufficient volume to enclose the object. The basket is then positioned until the object is within the basket. The wires are then retracted into the sheath shrinking the volume and pulling the object against the end of the sheath. The smaller the object, the more wires are needed to trap and hold the object. Conversely, large stones will not be able to work their way between closely spaced wires for capture.

Surgical instruments of the prior art have important limitations. First, they are mechanically complex, particularly mechanical baskets, and are therefore difficult, time-consuming and expensive to manufacture. Second, positioning such prior art surgical instruments to effectively grasp the object to be removed is difficult. This is particularly true where the surgical procedure requires a surgical device which can capture or remove objects with a capturing portion which is generally perpendicular to the longitudinal axis of the surgical device. One example of such a procedure is where the object to be captured or removed is present in a blood vessel or is a kidney stone present in the ureter. Third, positioning such prior art surgical instruments extends the duration of the surgery and increases the risk to the patient. Fourth, where wires of sufficient elastic strength to open and close about an object are used, the rigidity of such wires contributes to trauma of sensitive tissue surrounding the object to be captured or removed during positioning. Fifth, where the surgical instrument includes a sack for capturing objects to be removed, the sack cannot be emptied in the body canal, cavity or organ. Hence, once captured, the object and sheath must be removed from the body canal, cavity or organ regardless of the trauma thereto. This is particularly true when the size of the object is greater than the size of the body canal, cavity or organ, or the openings therein, through which the object is to be removed.

It is an object of the present invention to provide a surgical device capable of capturing and removing an object from body canals, cavities and organs which is not mechanically complex, is easily positionable and will minimize trauma to sensitive tissue surrounding the object to be captured or removed. It is an object of the present invention to provide a surgical device which is relatively easy to manufacture and which has a capturing portion positionable generally perpendicular to a longitudinal axis of the surgical device. It is an object of the present invention to provide a surgical device which includes for capturing an object a sack which can be emptied inside a body canal, cavity or organ.

SUMMARY OF THE INVENTION

Accordingly, we have invented an instrument for manipulating an object in a body canal, cavity or organ. The instrument includes a handle, a linkage having a proximal end and a distal end, an actuator attached between the handle and the proximal end of the linkage for extending and retracting the linkage, and a sheath attached to the handle having the linkage slidably received in a bore thereof. Attached to the distal end of the linkage is a proximal end of a frame which has a distal end extendable from and retractable into the sheath by the actuator. The frame is formed of a shape-memory-effect material trained to form at least a partial loop when extended beyond the sheath. The frame includes a pair of control arms that are positioned in the bore of the sheath when the frame is retracted into the sheath and which diverge from the bore to the at least partial loop when the distal end of the frame is extended beyond the sheath. The at least partial loop is formed continuous between the pair of control arms. The instrument includes a sack having a rim or mouth attached to the at least partial loop and a closed end disposed opposite the mouth. The mouth of the sack is opened and closed when the pair of control arms are extended from and retracted into the sheath. An invertor is provided for urging the closed end of the sack towards the mouth of the sack.

Preferably, the invertor includes a filament extending through the mouth of the sack and connected to the closed end of the sack. The filament preferably extends between the closed end of the sack and the handle through the bore of the sheath. The end of the filament opposite the closed end of the sack is manipulatable independent of the handle so that pulling the end of the filament opposite the closed end of the sack causes the filament to pull the closed end of the sack toward the mouth thereof. The sack is preferably formed from mesh-like material that can capture and retain the object while allowing fluids to pass therethrough.

We have also invented an instrument for removing an object from a body canal, cavity or organ. The instrument includes a sheath having a central bore, a frame slidably received in the bore of the sheath and having an end extendible from or retractable into the bore. The end of the frame is formed from a shape-memory-effect material trained to form at least a partial loop when extended from the sheath. The at least partial loop extends between a pair of control arms that diverge from the end of the bore to the at least partial loop when the end of the frame is extended from the bore. The instrument also includes a sack and an invertor. The sack has a mouth that is attached to the at least partial loop and the invertor is utilized for urging a closed end of the sack toward the mouth of the sack.

Preferably, the at least partial loop is receivable in the bore when the end of the frame is retracted into the bore. The mouth of the sack is open when the frame is extended from the bore and closed when the end of the frame is retracted into the bore.

We have also invented a surgical instrument that includes a frame that is adjustable between an open state and a closed state and a sack having attached to the frame a mouth that is openable and closeable with adjustment of the frame between the open and closed state. An invertor is provided for urging the closed end of the sack through the mouth of the sack.

BRIEF DESCRIPTION OF THE DRAWINGS

FIG. 7 is a view of the surgical device of FIG. 2 with the sack retracted into the sheath;

FIG. 8 is a view of a mouth end of the sack of FIG. 2 with tabs disposed around the mouth thereof;

FIG. 9 is an isolated view of the sack and wire frame of FIG. 2 including cut-out portions around the mouth of the sack;

DETAILED DESCRIPTION OF THE INVENTION

Figure 1:
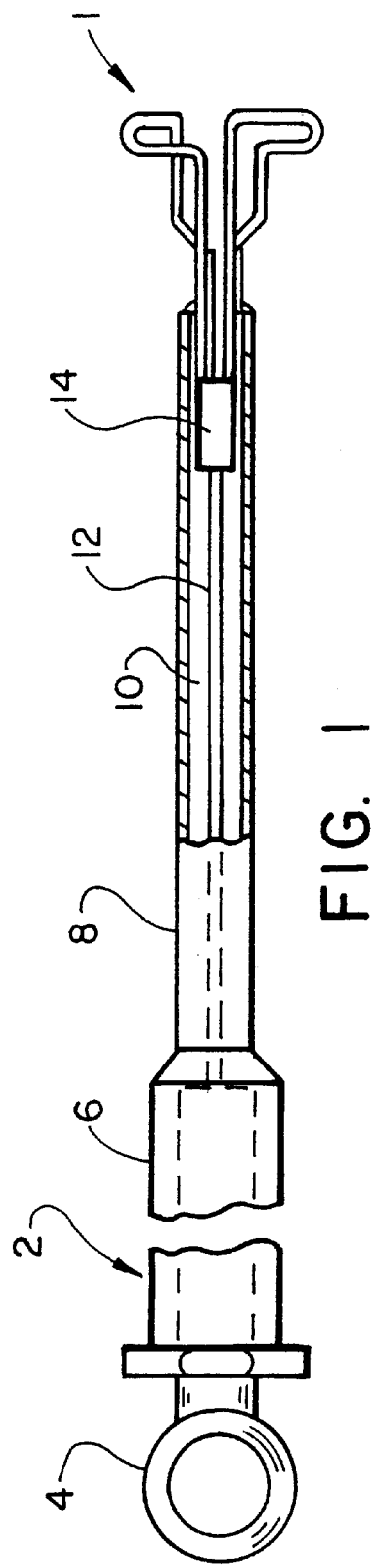
FIG. 1 is a partial cross-sectional side view of a surgical device for removing an object from a body canal, cavity or organ according to the present invention including a wire frame extended from a sheath.

Referring to FIG. 1, a surgical device 1 for capturing and removing an object from an organ, canal or cavity in a body includes a handle 2 which functions to position the surgical device 1 in the body. Preferably, the handle is a syringe-type handle which induces plunger 4 received in a cylinder 6. Alternatively, however, the handle 2 may be a pistol-like grip. An elongated tubular sheath 8 is attached to the cylinder 6. The sheath 8 and the cylinder 6 cooperate to form a lumen or bore 10 therethrough. Sheath 8 can be made of any flexible biocompatible material, including polyethylene, nylon or polyimides. Polyethylene is preferred because its surface has the least friction permitting easy travel of a wire linkage 12, a wire frame 14 and a sack 16 within the sheath 8. Polyimides generally have higher dimensional stability, however, they are less lubricious than polyethylenes.

Figure 2:
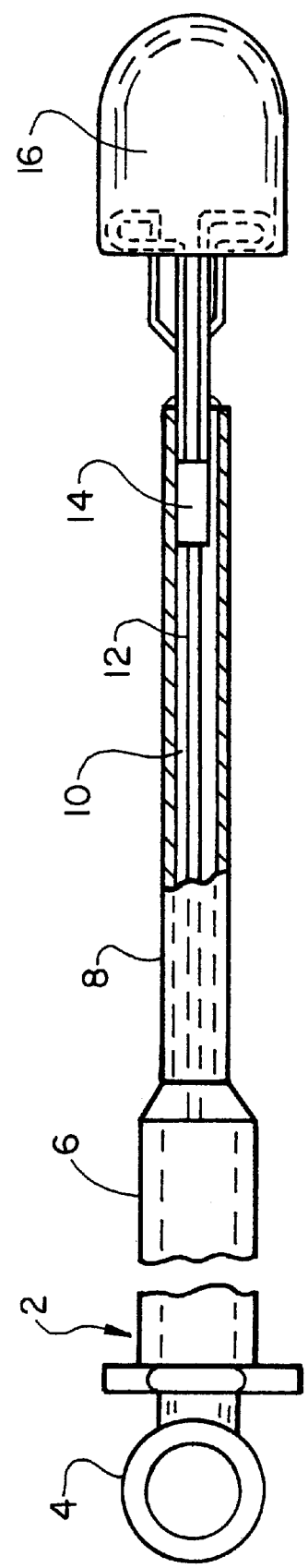
FIG. 2 is a view of the surgical device of FIG. 1 with a sack attached to the wire frame.

The wire linkage 12 has a first end attached to the plunger 4 and a second end attached to the wire frame 14. The wire linkage 12 may be a shape-memory-effect alloy in the super elastic state or another biocompatible metal or alloy. As shown in FIG. 2, attached to the wire frame 14 is the sack 16 which is utilized to capture an object from a body canal, cavity or organ.

Figure 3:
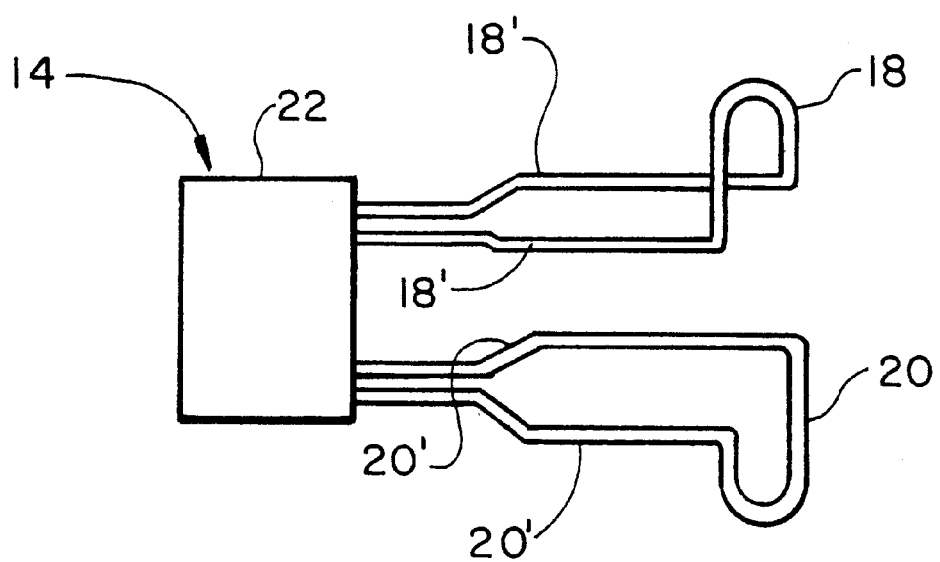
FIG. 3 is an isolated view of the wire frame of FIG. 1 including two halves of the wire frame in a deployed state.

Referring to FIG. 3, the wire frame 14 includes a half frame 18 and a half frame 20 joined at a proximal end of the wire frame 14 by a junction 22. The junction 22 is preferably a crimp of biocompatible material that is utilized to join and maintain the relative orientations of the half frames 18 and 20. The half frames 18 and 20 in their deployed state, form at least a partial loop at a distal end of each half frame. Each partial loop is preferably oriented generally perpendicular to a longitudinal axis of the wire linkage 12, as shown in FIGS. 1 and 2. Each half frame 18, 20 includes a pair of control arms 18', 20' that diverge from the bore 10 of the sheath 8 to the at least partial loop thereof. Each partial loop is formed continuous between its pair of control arms.

Figure 4:
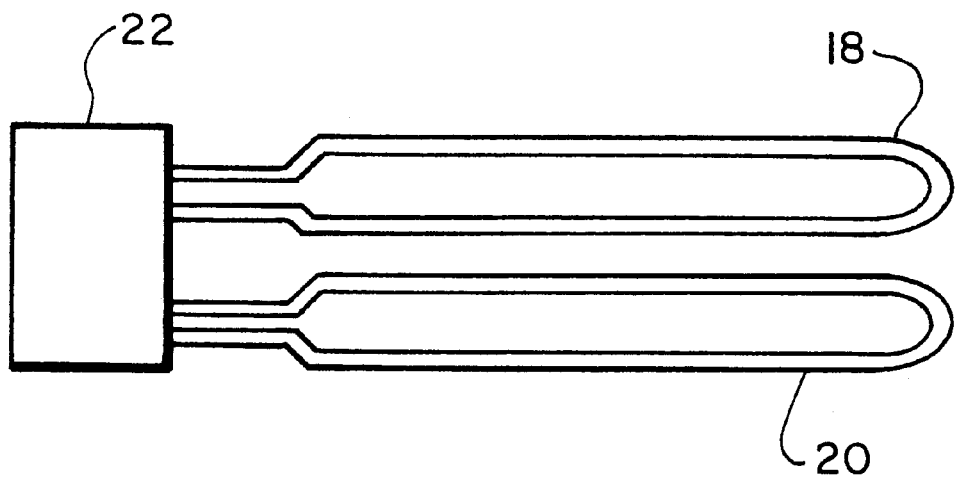
FIG. 4 is an isolated view of the wire frame of FIG. 3 with the two halves of the wire frame in a retracted state.
Figure 5:
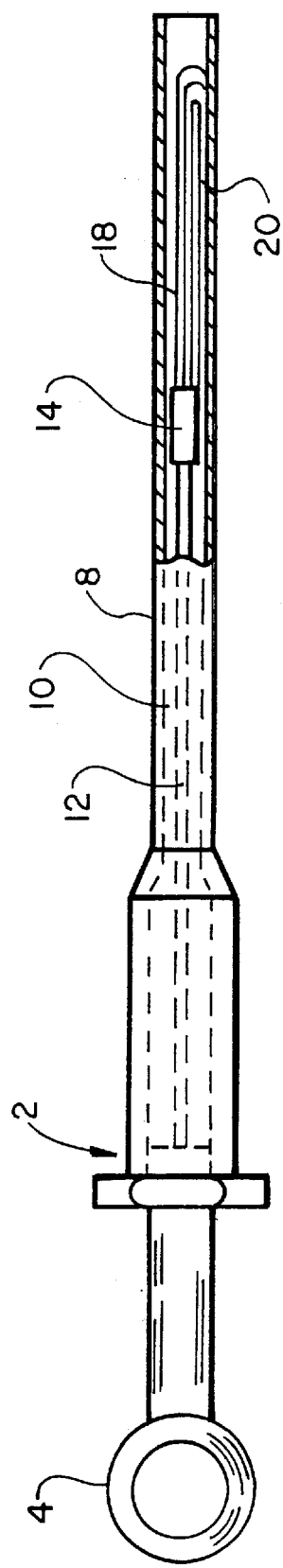
FIG. 5 is a view of the surgical device of FIG. 1 with the retracted wire frame halves of FIG. 4 received in the sheath.

Referring to FIGS. 4 and 5, half frame 18 and half frame 20 are each constructed from a shape-memory-effect alloy in the super elastic state. An example of such a shape-memory-effect alloy of Nitinol®. Nitinol® is a registered trademark of Minnesota Mining and Manufacturing Company of Saint Paul, Minn. The half frames 18 and 20 have been "trained", by processes known in the art with respect to shape-memory-effect alloys, to form the control arms 18', 20' and the partial loops described above. As shown in FIG. 7, when retracted into the bore 10 of the sheath 8, the half frames 18, 20 are mechanically stressed within their elastic limits to form long narrow loops 26 and 28 substantially parallel to the longitudinal axis of the wire linkage 12.

Because the shape-memory-effect alloy can "learn" a given shape, the partial loops of half frames 18 and 20 can be used in body lumens and canals. More specifically, the deployment of the partial loops of half frames 18 and 20 within a body lumen opens the mouth of the sack 16 substantially coextensive with the diameter of the lumen, assuring complete capture of an object therein. This is particularly valuable where the object to be captured or removed is given to fragmentation. Moreover, the shape-memory-effect alloy obtains the desired shape with a minimum of force and remains firm and pliable. The firm and pliable nature of the shape-memory-effect alloy produces little or no trauma to the tissues surrounding the object to be captured or removed. More specifically, the shape-memory-effect alloy displaces soft tissue as necessary and allows for significant back pressure from such soft tissue. In contrast, formed elastic steels of the prior art forcibly deform such soft tissue, regardless of the soft tissues' back pressure, resulting in far more trauma to the soft tissue forcibly deformed thereby.

The wire linkage 12 and/or the wire frame 14 may be coated with a material to form a thin, tough, flexible, lubricious coating thereon. One example of such a material is parylene, a synthetic material available from Specialty Coating Systems of Indianapolis, Ind. Alternatively, the inside surface of the tubular sheath 8 can be modified to reduce drag on the wire linkage 12, the wire frame 14, and the sack 16. In one embodiment, the inside surface of tubular sheath 8 is coated with a biocompatible lubricant, such as silicon. Alternatively, the inside surface of sheath 8 can be coated with a hydrophylic film.

Figure 6:
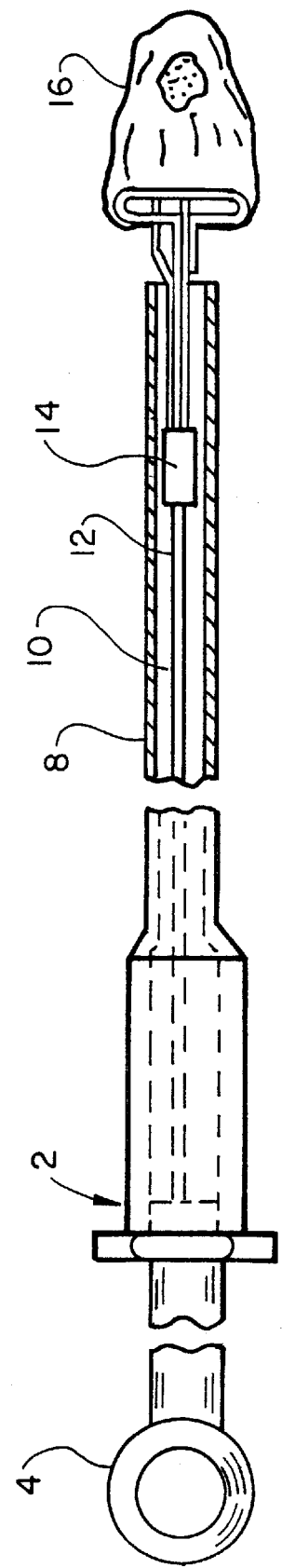
FIG. 6 is a view of the surgical device of FIG. 2 with an object captured in the sack.

The sack 16 is formed from a biocompatible material having sufficient strength to ensnare and retain an object within the sack, as shown in FIG. 6. Preferably, the sack 16 is formed of a polymeric material, and more specifically, an elastomeric polyurethane. However, the sack 16 may also be formed from a woven polyester fabric. A rim or mouth of the opening of sack 16 is preferably bonded to the partial loop portions of half frames 18 and 20 to secure the sack 16 to the wire frame 14. The bonding may be a chemical adhesive or a heat based bonding, or both. Alternatively, as shown in FIG. 8, the sack 16 may be formed with a plurality of tab-like projections 24 wrappable around half frames 18 and 20 and bondable thereto as described above. The sack 16 may also be coated with a thin, tough, flexible, lubricious coating, such as parylene.

The size of the lumen of the organ, canal or cavity in which the object sought to be surgically removed is found will typically determine the dimensions of the deployed half-loop portions of the wire frame 14 to be utilized therein. Similarly, the length of sheath 8 and the length of wire linkage 12 are determined by the position of the organ, canal or cavity, and by the position of the object in the organ, canal or cavity, relative to an entry site therein. In one embodiment, the wire frame 14 has a diameter of approximately 0.008 and the plastic sheath 8 has a diameter of 0.039 inches and an inside diameter that it can accommodate the wire frame 14 and the sack 16 in the retracted position shown in FIG. 7.

In use, the surgical device 1 is inserted into an organ, canal or cavity through an opening therein with the wire frame 14 and the sack 16 fully retracted in the sheath 8. The end of the surgical device 1 opposite the handle 2 is positioned at a point beyond the object to be removed or captured with respect to the opening in the body canal, cavity or organ. The wire frame 14 and the sack 16 are then extended beyond the sheath 8. As shown in FIGS. 6 and 7, the distal end of wire frame 14 is extended beyond the sheath 8 by pushing plunger 4 inwardly into cylinder 6, whereupon the wire linkage 12 causes the distal end of the wire frame 14 to extend beyond sheath 8, whereupon the partial loops of the half frames 18 and 20 assume their "learned" super elastic shape.

When the half frames 18 and 20 assume their "learned" shapes, the generally partial loops are formed, thereby holding the mouth of the sack 16 in an open position coextensive with the circumference of the body lumen. A circumference coextensive with the body lumen is preferred because as the surgical device 1 is drawn back toward the object to be captured or removed, the object will be readily captured within the sack 16. However, the partial loops of half frames 18 and 20 can be utilized to form an opening for the mouth of the sack 16 of a circumference less than that of the body lumen.

Figure 10:
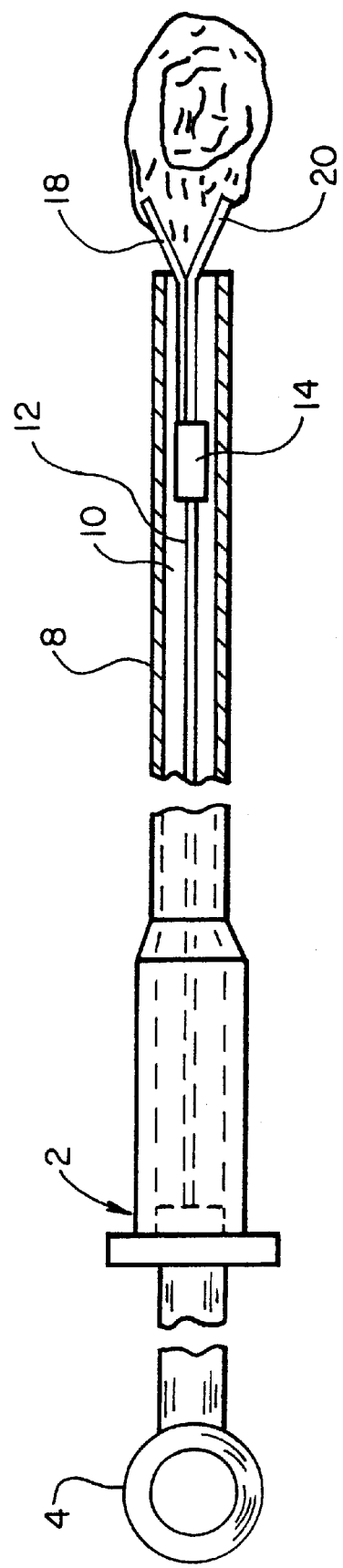
FIG. 10 is a view of the surgical device of FIG. 6 with the wire frame partially retracted into the sheath.

When the object is within the sack 16, the wire frame 14 is retracted into the bore 10 of the sheath 8 to fully encircle and capture the foreign object. More specifically, as shown in FIG. 10, pulling the plunger 4 out from the cylinder 6 causes the wire frame 14 and the sack 16 to re-enter the bore 10 of the sheath 8 and return to the position as shown in FIG. 7. If the object captured has a larger diameter than the bore 10 of the sheath 8, the distal end of the wire frame 14 and the sack 16 cannot be retracted into the sheath 8. In this case, the plunger 4 is pulled out from cylinder 6 to a point where the resistance felt, preferably aided by the direct, endoscopic, fluoroscopic, or other visualization, indicates that the object is safely retained within sack 16. At that point, the surgical device 1 is removed from the organ, canal or cavity with the object captured within the sack 16.

Referring to FIG. 9, it has been observed that retracting the distal end of the sack 16 into the sheath 8 causes the material of the sack 16 to bunch at its interface with the bore 10 of the sheath 8. To avoid this bunching, the sack 16 is preferably formed with one or more cut out portions 30 and 32. These cut out portions 30 and 32 avoid bunching of sack 16 as it is retracted into the bore 10 of the sheath 8.

Figure 11:
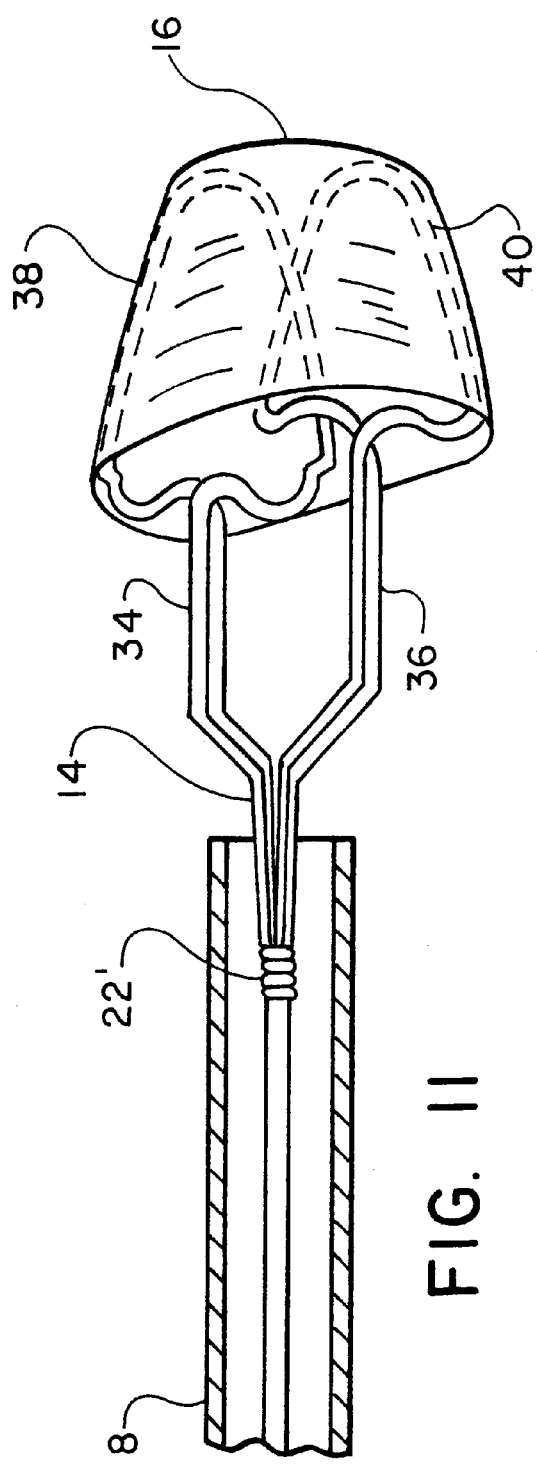
FIG. 11 is a view of the sheath of FIG. 1 including a slightly modified wire frame received therein.
Figure 12:
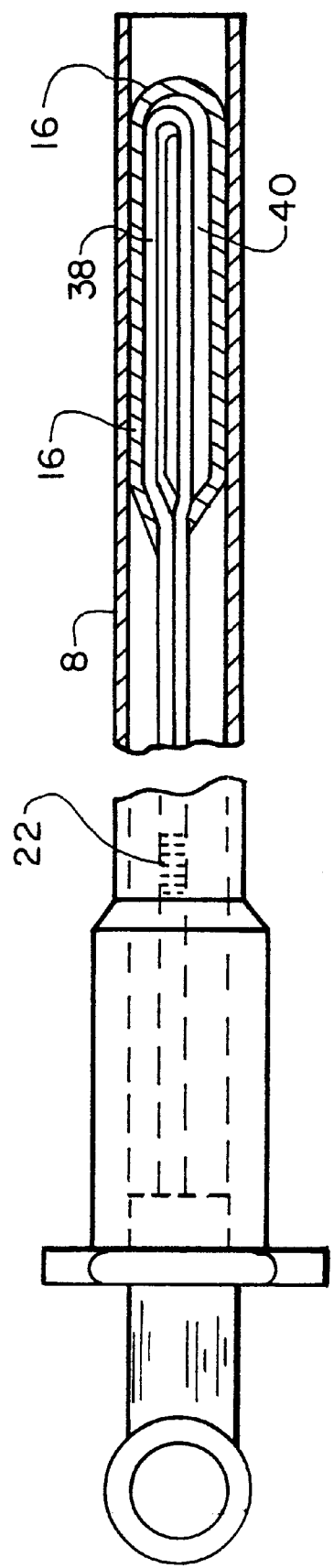
FIG. 12 is a partial cross-sectional view of the surgical device of the present invention showing the slightly modified wire frame of FIG. 11 retracted in the sheath.

Referring to FIG. 11, another embodiment that avoids bunching of the sack 16 includes the wire frame 14 having the junction 22 and frame members 34 and 36. Frame members 34 and 36 differ from half frames 18 and 20 in that they each include an elongated arch 38 and 40 respectively, shown in phantom in FIG. 11. The elongated arches 38 and 40 perform three functions. First, when the frame members 34 and 36 are extended beyond the sheath 8, the arches 38 and 40 hold the sack 16 in an open position. Second, when retracted into the sheath 8, the arches 38 and 40 prevent sack 16 from bunching. Third, when extended beyond the sheath 8, the arches 38 and 40 urge the bottom of the sack 16 out of sheath 8, further preventing bunching of the sack 16. Frame members 34 and 36, like control arms 18' and 20', extend along the longitudinal axis of sheath 8 and diverge when the wire frame 14 is extended from the sheath 8.

Figure 13:
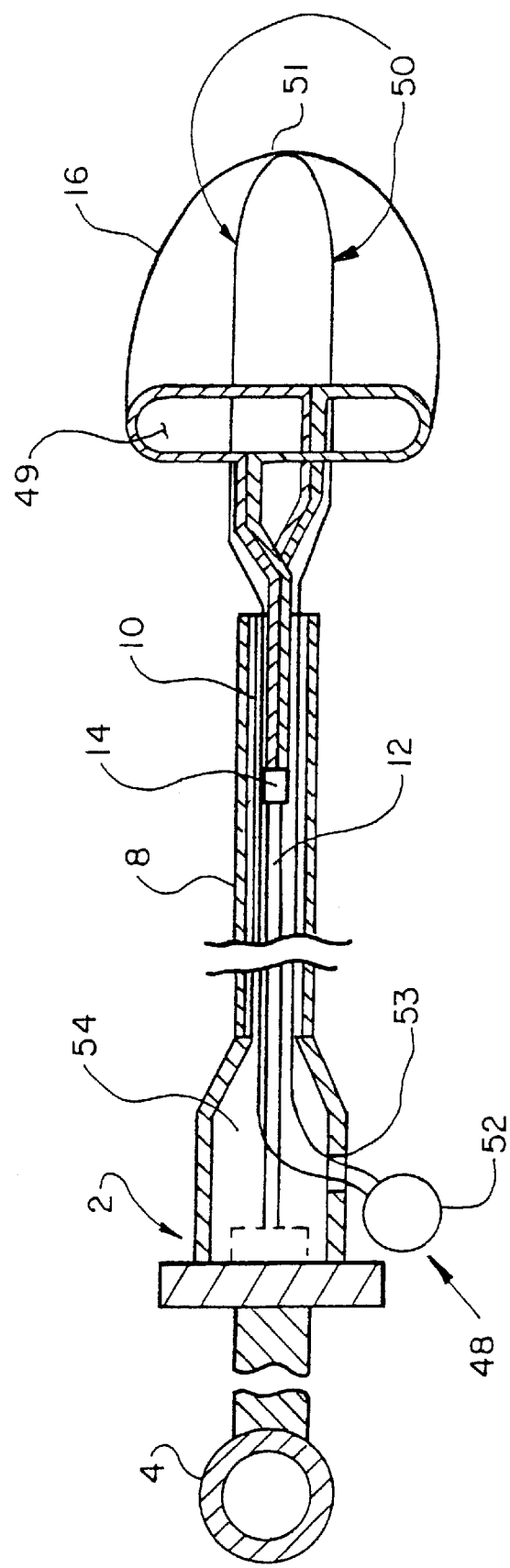
FIG. 13 is a cross-sectional view of the surgical device of FIG. 2 including a filament disposed in a bore of the sheath and connected to a closed end of the sack opposite the mouth.

With reference to FIG. 13, emptying the sack 16 may be desirable in certain instances, such as kidney stone extraction, where it is discovered after the object is captured in the sack 16 that the size thereof prohibits movement through an opening such as the ureter or opening into the bladder. Hence, it may be desirable to empty the object from the sack 16 in situ and remove the surgical device 1 thereby leaving the object in the organ, canal or cavity so that other procedures can be performed, such as shattering the object. To enable an object captured in the sack 16 to be emptied therefrom, the surgical device 1 includes an invertor 48 which is utilized to urge the closed end 51 of the sack 16 towards the mouth 49 thereof. The invertor 48 includes a filament 50, preferably made of fine wire, that is fixed to and around a closed end 51 of the sack 16. The filament preferably extends from the closed end 51 of the sack 16, through the mouth 49, through the lumen or bore 10 of sheath 8, into a cavity 54 of handle 2 and through an opening 53 formed in the handle 2. The end of the filament 50 opposite the end 51 of the sack 16 includes a gripping means 52, such as a ring.

If it is desired to empty a captured object from the sack 16, the mouth of the sack 16 is held in the open position by the partial loops of the wire frame 14 in a deployed state and the gripping means 52 is pulled away from handle 2 thereby causing filament 50 to pull or urge the closed end 51 of the sack 16 toward the mouth 49. Pulling the closed end 51 of the sack 16 toward the mouth 49 causes the object captured in the sack 16 to be advanced through the mouth 49 and emptied from the sack 16. Pulling grasping means 32 sufficiently away from handle 2 causes the sack 16 to invert, however, it may not be necessary to completely invert the sack 16 to empty an object therefrom.

The surgical device of the present invention safely captures and removes foreign objects from body canals, cavities or organs under either direct, endoscopic, fluoroscopic or other visualization. For instance, the present invention may be used to remove calculi from the urinary tract and the common bile duct under endoscopic or fluoroscopic visualization. It may also be used to remove an object forcibly inserted into the ear or nose under direct visualization. It may even be used to retrieve a swallowed object under endoscopic visualization. The device of the present invention is easy to position and requires little positioning to capture foreign objects lodged in body organs, cavities or canals so as to expedite removal. Further, due to the nature of the firm but pliable shape-memory-effect alloy, minimal trauma will be effected on tissue surrounding the foreign object to be captured or removed. Moreover, the surgical device of the present invention enables a foreign object to be captured and thereafter, if desired, released in situ if necessary or desired to avoid withdrawing the object through an undesirably small opening in the organ, cavity or canal.

To those skilled in the art, many modifications and variations of the present invention are possible in light of the above teachings. It is, therefore, understood that the present invention can be practiced otherwise than as specifically described herein and still will be within the spirit and scope of the appended claims.

I claim:

1. An instrument for manipulating an object in a body canal, cavity or organ, the instrument comprising:

a first linkage having a proximal end and a distal end;

a sheath having the first linkage slidably received in a bore thereof;

a frame having a proximal end attached to the distal end of the first linkage, a distal end extendible from and retractable into the sheath by the first linkage and formed of a shape-memory-effect material trained to form at least a partial loop when extended beyond the sheath, and a pair of control arms that are positioned in the bore of the sheath when the frame is retracted into the sheath and which diverge from the bore to the at least partial loop when the distal end of the frame is extended beyond the sheath, the at least partial loop formed continuous between the pair of control arms;

a sack having a mouth attached to the at least partial loop and a closed end opposite the mouth, the mouth of the sack is opened and closed when the pair of control arms are extended from and retracted into the sheath; and a second linkage connected to the closed end of the sack and which extends therefrom through the mouth of the sack to an exterior thereof when the sack is opened for urging the closed end of the sack toward the mouth of the sack.

2. The instrument as set forth in claim 1, wherein the second linkage is utilized to urge the closed end of the sack toward the mouth of the sack when the mouth is open.

3. The instrument as set forth in claim 1, wherein the second linkage includes a filament extending through the mouth of the sack.

4. The instrument as set forth in claim 1, wherein:

the second linkage extends to the closed end of the sack through the bore of the sheath; and pulling the end of the second linkage opposite the closed end of the sack causes the second linkage to pull the closed end of the sack toward the mouth thereof.

5. The instrument as set forth in claim 1, wherein:

the handle is a syringe-type handle;

the actuator includes a plunger slidably received in a cylinder;

the proximal end of the first linkage is attached to the plunger; and the sheath is attached to the cylinder.

6. The instrument as set forth in claim 1, wherein the at least partial loop defines a plane that is substantially normal to the bore of the sheath.

7. The instrument as set forth in claim 1, wherein the frame is further comprised of a first half frame and a second half frame joined at a junction that is attached to the first linkage.

8. The instrument as set forth in claim 7, wherein the control arms cause the mouth of the sack to open when the distal end of the first linkage is extended from the sheath.

9. The instrument as set forth in claim 1, wherein the sack adjacent the mouth thereof includes a cut-out portion that prevents bunching of the sack when the sack is retracted into the bore.

10. The instrument as set forth in claim 1, wherein the sack is formed from mesh-like material that can capture and retain the object while allowing fluids to pass therethrough.

11. An instrument for removing an object from a body canal, cavity or organ, the instrument comprising:

a sheath having a central bore therethrough;

a frame slidably received in the bore of the sheath and having an end extendable from and retractable into the bore, the end of the frame formed from a shape-memory-effect material trained to form at least a partial loop when extended from the sheath, the at least partial loop extending between a pair of control arms that diverge from the end of the bore to the at least partial loop when the end of the frame is extended from the bore;

a sack having a mouth that is attached to the at least partial loop and a closed end opposite the mouth; and a linkage connected to the closed end of the sack and which extends therefrom through the mouth of the sack to an exterior thereof when the sack is opened for urging the closed end of the sack toward the mouth of the sack.

12. The instrument as set forth in claim 11, wherein:

the at least partial loop is receivable in the bore when the end of the frame is retracted into the bore;

the mouth of the sack is opened when the end of the frame is extended from the bore; and the mouth of the sack is closed when the end of the frame is retracted into the bore.

13. The instrument as set forth in claim 12, wherein in the absence of the object therein the sack is retractable into the bore.

14. The instrument as set forth in claim 11, wherein the linkage includes a filament extending through the mouth of the sack.

15. The instrument as set forth in claim 11, wherein the linkage is connected to the sack at a closed end thereof opposite the mouth.

16. A surgical instrument comprising:

a frame that is adjustable between a closed state and an open state;

a sack having attached to the frame a mouth that is closeable and openable with adjustment of the frame between the closed state and the open state; and a linkage connected to a closed end of the sack and which extends therefrom through the mouth of the sack to an exterior thereof when the sack is opened for urging the closed end of the sack through the mouth thereof attached to the frame.

17. The surgical instrument as set forth in claim 16, wherein the linkage urges the closed end of the sack through the mouth when the frame is in the open state.

18. The surgical instrument as set forth in claim 16, wherein the linkage includes a filament that extends through the mouth and is connected to the sack at the closed end thereof opposite the mouth.

19. The surgical instrument as set forth in claim 16, wherein the linkage is positioned adjacent an inside surface of the sack.

* * * * *